(12) United States Patent
Nozaki et al.

(10) Patent No.: US 9,173,787 B2
(45) Date of Patent: Nov. 3, 2015

(54) ABSORBENT ARTICLE

(75) Inventors: Satoshi Nozaki, Kanonji (JP); Tsutomu Shirai, Kanonji (JP); Toshiyuki Tanio, Kanonji (JP); Kiyoko Nishimura, Kanonji (JP)

(73) Assignee: UNICHARM CORPORATION, Shikokuchuo-shi (JP)

( * ) Notice: Subject to any disclaimer, the term of this patent is extended or adjusted under 35 U.S.C. 154(b) by 791 days.

(21) Appl. No.: 13/499,082

(22) PCT Filed: Aug. 27, 2010

(86) PCT No.: PCT/JP2010/065085
§ 371 (c)(1),
(2), (4) Date: Mar. 29, 2012

(87) PCT Pub. No.: WO2011/040177
PCT Pub. Date: Apr. 7, 2011

(65) Prior Publication Data
US 2012/0191055 A1    Jul. 26, 2012

(30) Foreign Application Priority Data
Sep. 30, 2009 (JP) ................................. 2009-228477

(51) Int. Cl.
*A61F 13/15* (2006.01)
*A61F 13/84* (2006.01)
*A61F 13/534* (2006.01)
*A61F 13/53* (2006.01)

(52) U.S. Cl.
CPC .............. *A61F 13/84* (2013.01); *A61F 13/534* (2013.01); *A61F 2013/530532* (2013.01)

(58) Field of Classification Search
CPC .............. A61F 13/15; A61F 13/15707; A61F 13/4704; A61F 13/475; A61F 13/476; A61F 13/49; A61F 13/49004; A61F 13/49007; A61F 13/51478; A61F 13/56
USPC ............ 604/291, 367, 368, 378–380; 607/96; 428/156, 159–161, 163, 165, 167–173
See application file for complete search history.

(56) References Cited

U.S. PATENT DOCUMENTS

2007/0156107 A1    7/2007 Kimura et al.

FOREIGN PATENT DOCUMENTS

CN         1985783       6/2007
EP         158914 A2 *  10/1985  ............. A41B 13/02
(Continued)

OTHER PUBLICATIONS

JP 7-238451 A (Miki et al), English machine translation of detailed description. (1995).*
(Continued)

*Primary Examiner* — Melanie Hand
(74) *Attorney, Agent, or Firm* — Morrison & Foerster LLP

(57) ABSTRACT

It is an object of the invention to provide an absorbent article that is resistant to twisting and flattening, and that is superior in terms of fluid absorption rate, fluid diffusibility, absorbed fluid retention volume and fluid retention. The absorbent article comprises a top sheet on the skin contact side, a back sheet on the non-skin contact side, and an absorbent body situated between the two sheets, wherein the absorbent body comprises a bulky absorbent sheet, and the bulky absorbent sheet comprises heat-expanding particles that are dispersed in the bulky absorbent sheet and have been expanded by heat.

8 Claims, 12 Drawing Sheets

66.6 μm

(56) References Cited

FOREIGN PATENT DOCUMENTS

| | | |
|---|---|---|
| EP | 2 281 942 | 2/2011 |
| EP | 2 292 839 | 3/2011 |
| JP | 7-238451 | 9/1995 |
| JP | 8-120567 | 5/1996 |
| JP | 2001-98494 | 4/2001 |
| JP | 2006-28654 | 2/2006 |
| JP | 2009-72420 | 4/2009 |
| JP | 2009-203586 | 9/2009 |

OTHER PUBLICATIONS

International Search Report mailed Nov. 30, 2010, directed to International Application No. PCT/JP2010/065085; 1 page.

Extended European Search Report dated Jun. 28, 2013, directed to EP Application No. 10820297.9; 5 pages.

\* cited by examiner

100 μm 66.6 μm

Fig.14
(a)
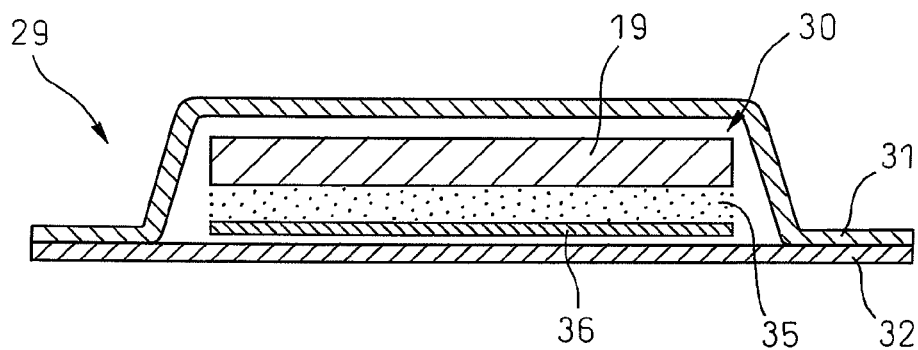
(b)
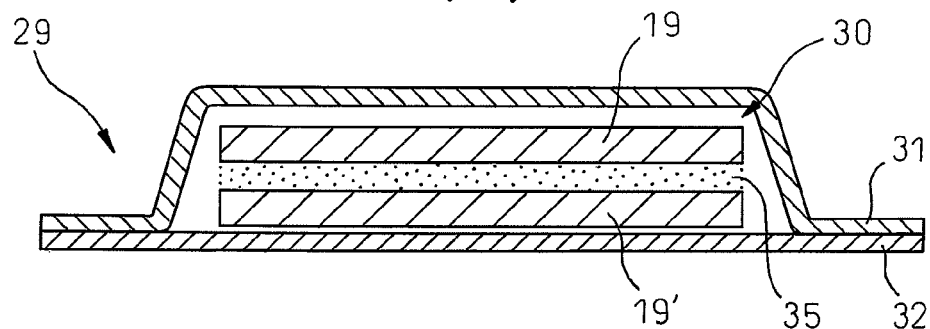
(c)
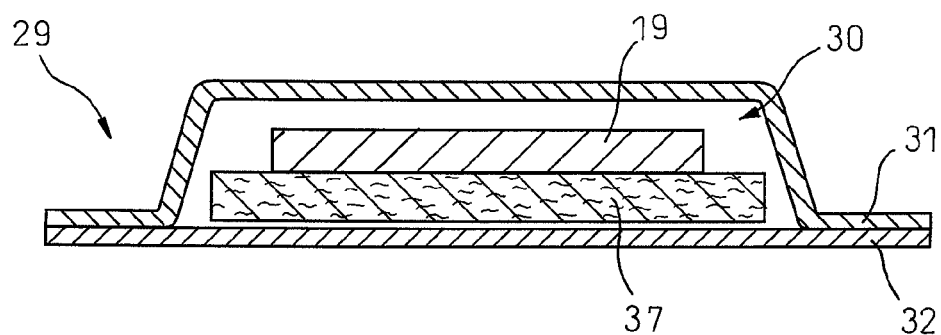

Fig. 15
(c)
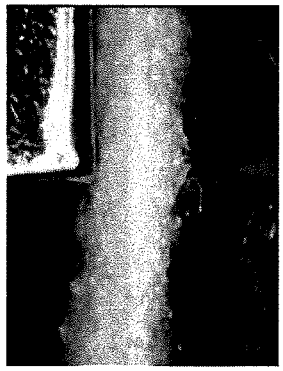
(b)
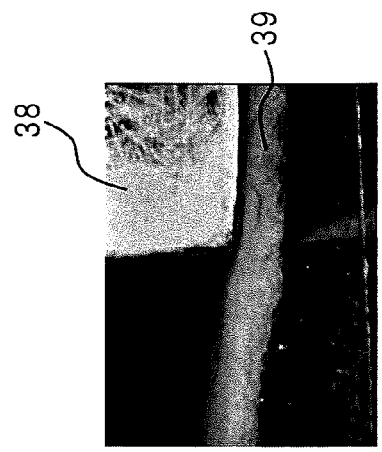
(a)

Fig.16
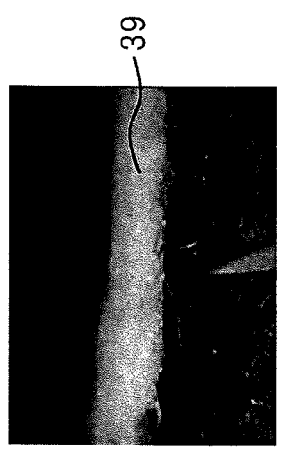
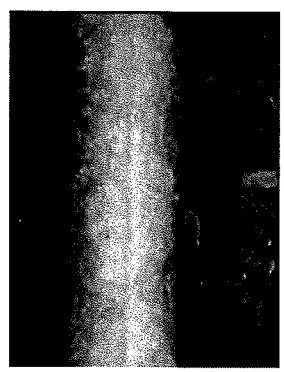

ABSORBENT ARTICLE

REFERENCE TO RELATED APPLICATIONS

This application is the national stage under 35 USC 371 of International Application No. PCT/JP2010/065085, filed Aug. 27, 2010, which claims priority from Japanese Patent Application No. 2009-228477, filed Sep. 30, 2009, the entire contents of which are incorporated herein by reference.

FIELD OF THE INVENTION

The present invention relates to an absorbent article. In particular, the invention relates to an absorbent article that is resistant to twisting and flattening, and that is superior in terms of fluid absorption rate, fluid diffusibility, absorbed fluid retention and fluid retention.

BACKGROUND OF THE INVENTION

Various improvements have been made in the properties of absorbent articles, such as sanitary napkins, paper diapers, incontinence pads and panty liners, including the "fluid absorption rate" relating to the speed of absorption of fluids, the "fluid diffusibility" relating to the ability of an absorbed fluid to diffuse through the entire absorbent body, the "absorbed fluid retention volume" relating to the amount of absorbed fluid that can be retained, and the "fluid retention" relating to the ability to retain absorbed fluids, for the purpose of preventing fluid leakage and reducing sticking of the absorbent article to the body, as well as the "low twisting" property.

Conventionally, absorbent sheets produced using natural pulp fiber as starting materials, and pulp fiber laminated sheets, such as fluff pulp sheets and dry pulp nonwoven fabrics, have been used as absorbent articles and especially as the materials of absorbent bodies, and it has been attempted to control the aforementioned properties by modifying the density of the absorbent body or employing super-absorbent polymer particles.

The absorbent sheet is generally prepared by wet paper forming and sheeting, and has a dense fiber layer structure. Such absorbent sheets are therefore considered to have strong capillary movement and excellent diffusibility for absorbed fluids. In actuality, however, such absorbent sheets do not exhibit satisfactory "fluid diffusibility" because they essentially lack voids between fibers, while they also lack a satisfactory "absorbed fluid retention volume" and "fluid absorption rate" because of the low degree of fluid retention.

Moreover, although the absorbent sheets have very high dry strength due to hydrogen bonding of cellulose, since the pulp fibers are densely layered, the absorbent sheets lose the hydrogen bonding between cellulose fibers when in a wet state, such that the wet strength becomes essentially zero, resulting in twisting and tearing during use. While the wet strength can be increased by using wet strengtheners, the low thicknesses tend to result in deformation, or twisting tends to occur due to the lack of repulsion elasticity.

Fluff pulp has a loose fiber layer structure with very weak bonding strength between fibers and numerous voids between fibers. Therefore, fluff pulp has a very high "fluid absorption rate" and a large "absorbed fluid retention volume", but conversely to the aforementioned absorbent sheets, its voids between fibers are too large, resulting in inferior "fluid diffusibility".

Such fluff pulp has elasticity in a dry state as well, but it also lacks any appreciable bonding strength between fibers, and therefore exhibits low strength and is prone to deformation, tearing and twisting during use.

Moreover, fluff pulp decreases in bulk when wetted by absorbed fluids, and application of body pressure tends to cause further reduction in bulk and to result in a very low absorption space. Therefore, since body fluids that have been absorbed and retained flow back to the body side and cause sticking and leaking, such pulp is inferior in terms of "fluid retention".

Dry pulp nonwoven fabrics are nonwoven fabrics produced by layering pulp fibers into a sheet in air and bonding the fibers together with a binder, and they have high wet strength, as well as a loose fiber built-up structure with a relatively large number of voids between fibers. Thus, the "absorbed fluid retention volume" is high upon wetting; however, the pulp fibers swell and soften and readily undergo deformation upon application of body pressure, and absorbed and retained body fluid returning back to the body side causes sticking and leaking, such that twisting or deformation tends to occur during use, similar to fluff pulp, and therefore the "fluid retention" is poor.

Fiber starting materials other than natural pulp fiber include bulky crosslinked cellulose fiber, comprising cellulose fiber with a fiber roughness of 0.3 mg/m or greater that has been crosslinked within and/or between molecules with a crosslinking agent, as disclosed in PTL 1. The crosslinked cellulose fiber disclosed in PTL 1 has low swelling when wet and is resistant to twisting and flattening, and is therefore useful as an absorbent body for absorbent articles.

Because the crosslinked cellulose fiber disclosed in PTL 1 is fibrous similar to natural pulp fibers, it must be worked into a form, such as an absorbent sheet, fluff pulp or dry pulp nonwoven fabric, similar to natural pulp fiber, when it is to be used as an absorbent body for an absorbent article.

PATENT LITERATURE

PTL 1 Japanese Unexamined Patent Publication No. 8-120567

SUMMARY OF INVENTION

The crosslinked cellulose fiber described above has strong elasticity of the fiber itself, compared to common cellulose fiber, such as pulp, and the fiber swelling property when wet is low due to the crosslinking, making the bulk relatively easy to maintain compared to natural pulp fiber, but when it is subjected to high stress, such as body pressure or the like, the bulk cannot be maintained by the characteristic elasticity and hardness of the fibers, and as a result, it tends to exhibit twisting and flattening similar to laminated sheets of common cellulose fiber, such as natural pulp, and the "fluid retention" is inferior.

It is therefore an object of the present invention to provide an absorbent article that is resistant to twisting and flattening, and that is superior in terms of fluid absorption rate, fluid diffusibility, absorbed fluid retention volume and fluid retention.

As a result of diligent research directed toward solving the problems described above, the present inventors have found that the problems can be solved by an absorbent article comprising a top sheet on the skin-contacting surface, a back sheet on the non-skin-contacting surface, and an absorbent body situated between the two sheets, wherein the absorbent body comprises a bulky absorbent sheet, the bulky absorbent sheet comprising heat-expanding particles that are dispersed in the bulky absorbent sheet and have been expanded by heat, and the invention has been completed upon this finding.

Specifically, the present invention relates to the following aspects.

[Aspect 1]

An absorbent article comprising a top sheet on the skin-contacting surface, a back sheet on the non-skin-contacting surface, and an absorbent body situated between the two sheets:

wherein the absorbent body comprises a bulky absorbent sheet, and the bulky absorbent sheet comprises heat-expanding particles that are dispersed in the bulky absorbent sheet and have been expanded by heat.

[Aspect 2]

The absorbent article according to aspect 1, wherein the bulky absorbent sheet is a bulky absorbent sheet with a density of 0.025-0.1 $g/cm^3$, obtained by a production method comprising the steps of:

forming a wet blended sheet comprising the heat-expanding particles dispersed in the fiber starting material from a paper-making starting material in which a fiber starting material comprising 30-100 mass % of natural pulp and 0-70 mass % of other fiber, and heat-expanding particles with a mean particle size of 5-30 μm are dispersed in water at a proportion of 5-30 parts by mass of the heat-expanding particles per 100 parts by mass of the fiber starting material, and then expanding at least some of the heat-expanding particles by heat to a 20-125 fold volume, to obtain a bulky absorbent sheet.

The absorbent article according to aspect 2, wherein the heating is carried out by moist hot air or water vapor, and the expanding step is further followed by a step of drying the wet blended sheet.

The absorbent article according to any one of aspects 1 to 3, wherein the bulky absorbent sheet has a concavoconvex pattern consisting of one or more high-basis-weight regions and one or more low-basis-weight regions.

The absorbent article according to aspect 4, wherein the one or more low-basis-weight regions are interspersed within the high-basis-weight region.

The absorbent article according to any one of aspects 1 to 5, wherein the bulky absorbent sheet has a concavoconvex pattern consisting of one or more low density regions with a high degree of expansion of the heat-expanding particles, and one or more high density regions with a low degree of expansion of the heat-expanding particles.

The absorbent article according to any one of aspects 1 to 6, wherein the Klemm water absorption degree of the bulky absorbent sheet is at least 10 mm, the percentage reduction in wet compressive bulk is no greater than 50%, and the wet compressive residual strain is no greater than 30%.

The absorbent article according to any one of aspects 1 to 7, wherein the absorbent body has a multilayer structure, and the uppermost layer on the top sheet side is the bulky absorbent sheet layer.

The absorbent article according to aspect 8, wherein the multilayer structure is composed of 3 or more layers, and at least one of the interlayers is a super-absorbent polymer layer.

The absorbent article according to aspect 9, wherein the lowermost layer is the bulky absorbent sheet or water-resistant tissue paper layer.

The absorbent article of the invention has an excellent fluid absorption rate and excellent fluid diffusibility, because the spaces between the expanded heat-expanding particles and the fibers, and the spaces between the fibers form voids, suitable for diffusion of fluids in the bulky absorbent sheet.

In addition, the absorbent article of the invention has excellent absorbed fluid retention volume because the volume of the aforementioned voids in the bulky absorbent sheet is greater than that in a conventional absorbent sheet.

Furthermore, the absorbent article of the invention has excellent fluid retention, and low leakage due to twisting and flattening, because the impact resilience of the expanded heat-expanding particles in the bulky absorbent sheet are resistant to twisting, and the original shape is rapidly restored even upon twisting.

BRIEF DESCRIPTION OF THE DRAWINGS

FIG. 14 is a cross-sectional view showing a variation example of an absorbent article according to the invention.

FIG. 15 is a telescope image of the cross-section of a specimen during measurement of the percentage reduction in wet compressive bulk in Example 1.

FIG. 16 is a telescope image of the cross-section of a specimen during measurement of the wet compressive residual strain in Example 1.

DETAILED DESCRIPTION OF THE INVENTION

The present invention will now be explained in greater detail, with the understanding that the invention is not limited to this explanation.

The bulky absorbent sheet used for the invention comprises heat-expanding particles that are dispersed in the bulky absorbent sheet, and are expanded by heat.

The bulky absorbent sheet used for the invention is a sheet in which a plurality of expanded heat-expanding particles are dispersed in an absorbent sheet, and it differs from a bulky structure formed by maintaining spaces by the coupled structure of the fibers themselves, as in a conventional bulked sheet. Thus, even when a compressive load is applied to the bulky absorbent sheet in a wet state in which the hydrogen bonds between fibers have been broken, the expanded heat-expanding particles exhibit elasticity against the load and bulk can be maintained. Consequently, the absorbent body is resistant to twisting, flattening and the like, and little of the fluid that has been absorbed is squeezed out by subsequent compression.

In addition, the expanded heat-expanding particles are formed by thermal expansion after the non-expanded heat-expanding particles have been dispersed in the absorbent sheet, and therefore spaces are formed between the fibers by expansion of the heat-expanding particles. Therefore, the spaces between the expanded heat-expanding particles and the fibers and the spaces between the fibers form voids suitable for diffusion of fluid, and can provide both of the reciprocal properties of bulk and fluid diffusibility.

Figure 1:
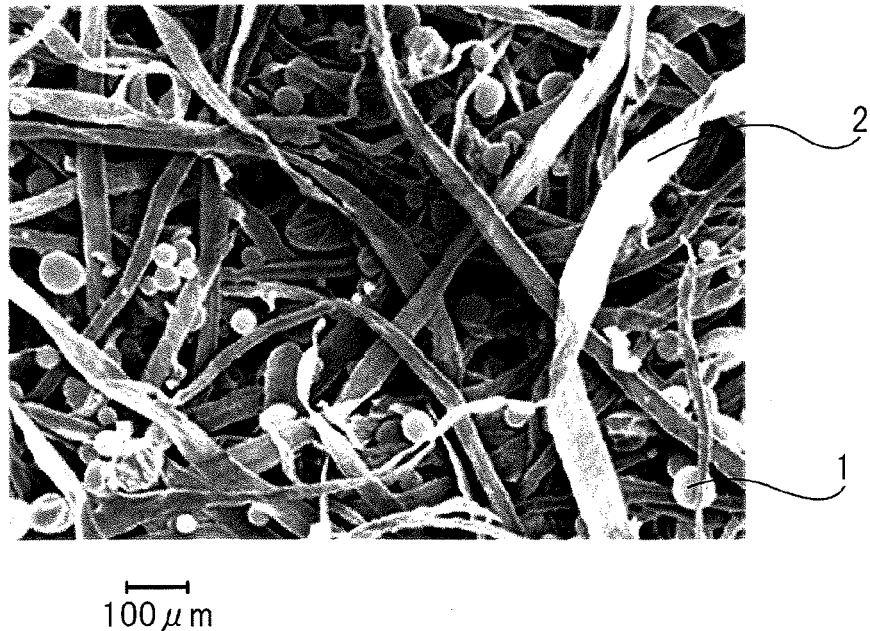
FIG. 1 is an electron micrograph of the front side of the bulky absorbent sheet 1 produced in Production Example 1.
Figure 2:
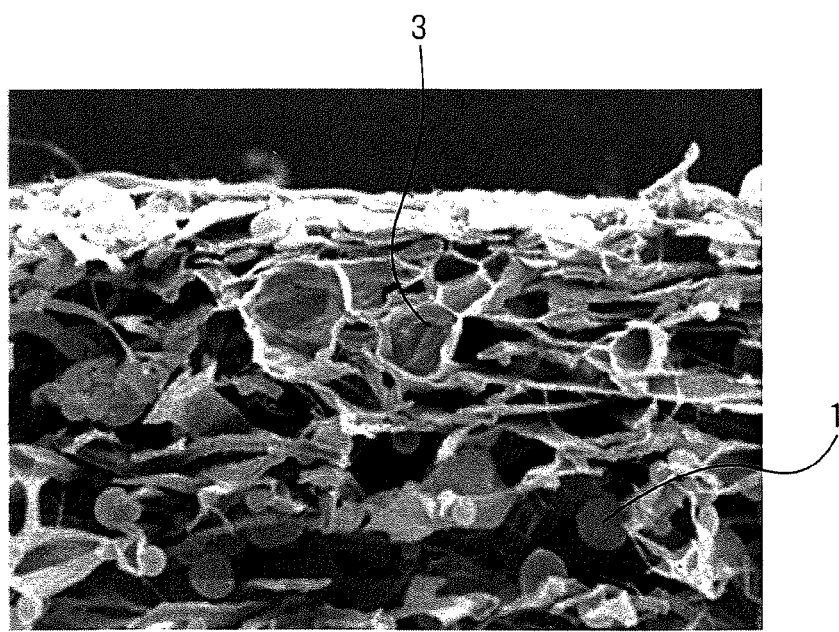
FIG. 2 is an electron micrograph of a cross-section of the bulky absorbent sheet 1 produced in Production Example 1.

FIG. 1 and FIG. 2 are electron micrographs of the front side and a cross-section of the bulky absorbent sheet produced in Production Example 1 described below.

The heat-expanding particles used for the invention are heat-expanding microcapsules obtained by encapsulating a low-boiling-point solvent in microcapsules formed from a film polymer. There are no particular restrictions on the particle size of the heat-expanding particles, but in consideration of the fluid absorption rate, fluid diffusibility, absorbed fluid retention volume, fluid retention and twisting resistance of the bulky absorbent sheet, the mean particle size before expansion is preferably 5-30 μm and more preferably 8-14 μm. The low-boiling-point solvent generates a gas, by volatilization, for example, at a lower temperature than the softening temperature, such as lower than the glass transition temperature, of the film polymer.

As used herein, "mean particle size" means the particle size at 50% in the volume-based cumulative distribution, of the particle size distribution measured with a laser diffraction particle size distribution analyzer (for example, HEROS & RODOS by JEOL Corp.).

Also, the term "heat-expanding particles", as used herein, means particles before expansion, while "expanded heat-expanding particles" means the particles after expansion by heat or the like.

The heat-expanding particles expand preferably 20- to 125-fold and more preferably 50- to 80-fold by volume upon brief heating at a relatively low temperature of 80-200° C. If the volume expansion is less than 20-fold, spaces will not easily form between the fibers, and the fluid absorption rate, fluid diffusibility and absorbed fluid retention volume of the bulky absorbent sheet will tend to be inadequate. If the volume expansion is greater than 125-fold, the fluid diffusibility of the bulky absorbent sheet will tend to be insufficient, and the elasticity of the expanded expanding particles will tend to be reduced, leading to more twisting and flattening.

The low-boiling-point solvent may be a volatile organic solvent (expanding agent), such as isobutane, pentane, petroleum ether, hexane, a low-boiling-point halogenated hydrocarbon, methylsilane, or the like.

The film polymer may be a thermoplastic resin composed of a copolymer of vinylidene chloride, acrylonitrile, acrylic acid ester, methacrylic acid ester or the like, and upon heating the film polymer at above the softening point, the film polymer begins to soften causing the vapor pressure of the encapsulated low-boiling-point solvent to increase simultaneously, so that the film is pushed outward resulting in expansion of the capsules. The heat-expanding particles expand at relatively low temperature and in a short period of time to form closed cells, thus creating particles with excellent elasticity and relatively easy manageability, which are suitable for the present purpose.

As such heat-expanding particles there are known Matsumoto Microspheres F-36, F-30D, F-30GS, F-20D, F-50D and F-80D (product of Matsumoto Yushi-Seiyaku Co., Ltd.) and EXPANCEL WU and DU (product of Sweden, marketed by Japan Fillite Co., Ltd.), although there is no limitation to these.

The fiber starting material used for the invention may be any one commonly used in the field of paper-making, without any particular restrictions, and examples include natural pulp, synthetic pulp, organic fiber and inorganic fiber. The fiber starting material preferably comprises 30-100 mass % of natural pulp and 0-70 mass % of other fiber, and more preferably it comprises 50 mass %-100 mass % of natural pulp and 0-50 mass % of other fiber. This will result in excellent anchoring, yield and uniform dispersibility of the heat-expanding particles, as well as excellent uniformity and strength of the sheet.

The other fibers are preferably selected from the group consisting of synthetic pulp, organic fibers and inorganic fibers.

The other fibers used may be, for example, synthetic fibers with a low melting point, when a heat sealing property is to be imparted to the bulky absorbent sheet used for the invention, or combined fibers with a long fiber length (3-25 mm), when breaking resistance is to be imparted.

The natural pulp may be wood pulp, such as chemical pulp or mechanical pulp from a conifer and/or broadleaf tree, waste paper pulp, or nonwood natural pulp, such as hemp or cotton, although there is no restriction to these. As synthetic pulp there may be mentioned synthetic pulp obtained from polyethylene or polypropylene starting materials, although there is no limitation to these. As the organic fiber there may be mentioned acrylic fiber, rayon fiber, phenol fiber, polyamide fiber and polyethylene fiber, with no limitation to these. As the inorganic fiber there may be mentioned glass fiber, carbon fiber, alumina fiber and the like, with no limitation to these.

The preferred amount of the heat-expanding particles will vary depending on the purpose of use and is not particularly restricted, but generally speaking it is preferably 5-30 parts by mass, more preferably 8-25 parts by mass and even more preferably 10-15 parts by mass, with respect to 100 parts by mass of the fiber starting material. An amount of heat-expanding particles of less than 5 parts by mass with respect to 100 parts by mass of the fiber starting material will result in less expansion, while an amount of greater than 40 parts by mass will tend to be economically disadvantageous.

The preferred value for the density of the bulky absorbent sheet used for the invention will differ depending on the purpose of use and is not particularly restricted, but generally speaking the sheet preferably has a density of 0.025-0.1 g/cm$^3$ and more preferably a density of 0.03-0.07 g/cm$^3$. If the density is less than 0.025 g/cm$^3$ the wet strength will be reduced or the proportion of heat-expanding particles will be increased, which is economically disadvantageous, while if the density is greater than 0.1 g/cm$^3$ the absorbed fluid retention volume and stability against twisting deformation will tend to be inferior.

An anchoring agent which is commonly used in the paper-making industry may be added during production of the bulky absorbent sheet to be used for the invention, in order to anchor the heat-expanding particles to the fibers.

In order to increase the wet sheet strength, an internal wet strength agent commonly used in the paper-making industry may be added during production, in addition to the low-melting-point synthetic fiber. By adding a wet strength agent it is possible to increase the water resistance of the bulky absorbent sheet.

However, excessive addition of the aforementioned anchoring agent or wet strength agent may result in inhibition of hydrophilicity and loss of flexibility of the bulky absorbent sheet, and therefore the addition amounts must be adjusted according to the purpose.

If desired, various anionic, nonionic, cationic or amphoteric yield improvers, paper strength additives, sizing agents and the like may also be added to the bulky absorbent sheet to be used for the invention. Specifically, as paper strength additives and yield improvers there may be used organic compounds, such as polyacrylamide-based cationic, nonionic, anionic and amphoteric resins, polyethyleneimine and its derivatives, polyethylene oxide, polyamines, polyamides, polyamidepolyamine and its derivatives, cationic and amphoteric starch, oxidized starch, carboxymethylated starch, vegetable gum, polyvinyl alcohol, urea-formalin resin, melamine-formalin resin and hydrophilic polymer particles, and inorganic compounds including aluminum compounds, such as aluminum sulfate, alumina sol, basic aluminum sulfate, basic aluminum chloride and basic polyaluminum hydroxide, and ferrous sulfate, ferrous chloride, colloidal silica, bentonite or the like, either alone or in combinations.

Production of the bulky absorbent sheet to be used for the invention is not particularly restricted, but it may be accomplished in the following manner, for example.

Figure 3:
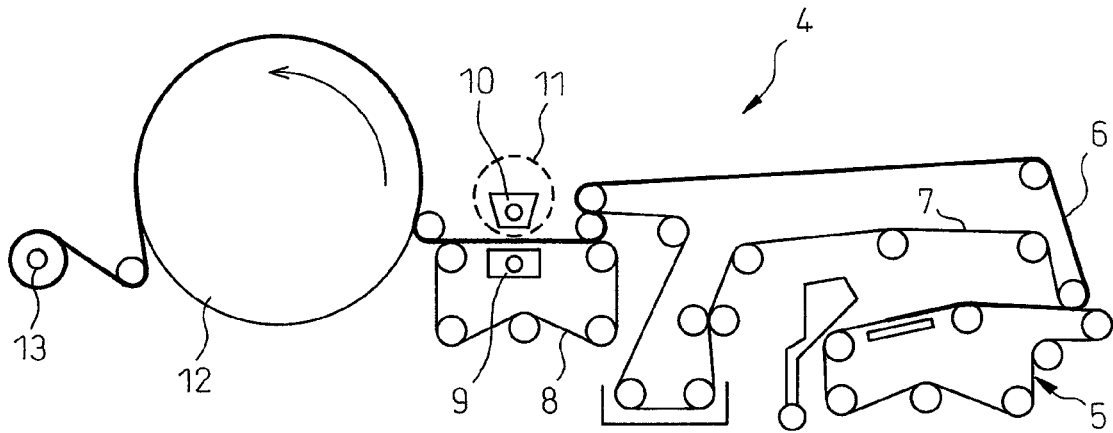
FIG. 3 is a schematic view of a paper machine that can produce a bulky absorbent sheet to be used for the invention.

FIG. 3 is a schematic view of a paper machine that can be used to produce a bulky absorbent sheet to be used for the invention. The paper machine 4 comprises a paper-making part 5, a wet blended sheet 6, a first conveyor belt 7, a second conveyor belt 8, a suction box 9, a jet nozzle 10, a screen 11, a dryer 12 and a finished product take-up roll 13. The wet blended sheet 6 is made by the paper-making part 5 from a paper-making starting material comprising a fiber starting material and heat-expanding particles dispersed in water, and the wet blended sheet 6 is conveyed by the first conveyor belt 7 and then dewatered by a press part.

In common paper-making steps, the water content of the wet blended sheet is adjusted to about 60 mass % by the dehydration step.

The dewatered wet blended sheet is conveyed by the second conveyor belt 8, and heated by spraying of hot air or the like from the jet nozzle 10 to expand the heat-expanding particles. If the dewatered wet blended sheet is placed on a support and suction is applied from the suction box 9 from the bottom side of the support while spraying the hot air from the top side, the entire sheet will be heated rapidly and evenly, thereby increasing the thermal expansion effect and raising efficiency. The support may be, but is not limited to, a net or other type of conveyor belt.

If desired, the sheet may be dried by the dryer 12 and the bulky absorbent sheet taken up on the finished product take-up roll 13. Expansion of the heat-expanding particles and drying of the bulky absorbent sheet may be accomplished simultaneously with the dryer 12, while eliminating spraying of hot air or the like from the jet nozzle 10.

As a separate embodiment for production of a bulky absorbent sheet to be used for the invention, moist hot air or water vapor at a prescribed temperature may be sprayed from the jet nozzle 10 to heat and expand the heat-expanding particles without drying the wet blended sheet. By using moist hot air or water vapor, the dewatered wet blended sheet does not dry even when excess heat is applied, for example, and it is possible to adequately expand the heat-expanding particles since no bonding strength is produced between fibers that would inhibit expansion of the heat-expanding particles. After the heat-expanding particles have been adequately expanded, the bulky absorbent sheet may be dried with the dryer 12.

When the thermal expansion step described above is accomplished by heating the dewatered wet blended sheet with moist hot air or water vapor at a prescribed temperature, the wet blended sheet is preferably dewatered to a low water content of, for example, 40-60 mass % in the dehydration step, in order to efficiently increase the temperature of the wet blended sheet as a whole to the prescribed temperature.

The temperature of the warm air, moist hot air or water vapor in the thermal expansion step is above the temperature at which the microcapsule shell walls of the heat-expanding particles soften and begin to expand, and it is a temperature determined by the heat-expanding particles used.

The humidity of the moist hot air or water vapor is preferably a high relative humidity, such as 100% RH, when the wet blended sheet is not dried in the thermal expansion step. The means for supplying the moist hot air or water vapor is most preferably means in which high-temperature steam from a boiler is ejected and directly sprayed onto the sheet, but humidified exhaust from a drier may also be used.

A bulky absorbent sheet having a concavoconvex pattern comprising one or more low density regions with a high degree of expansion of heat-expanding particles and one or more high density regions with a low degree of expansion of heat-expanding particles may be produced by spraying prescribed sections of a wet blended sheet with moist hot air or water vapor at above the initial expansion temperature of the heat-expanding particles to cause expansion of the heat-expanding particles at those sections, and subsequently drying at a temperature at which the heat-expanding particles do not fully expand.

Figure 4:
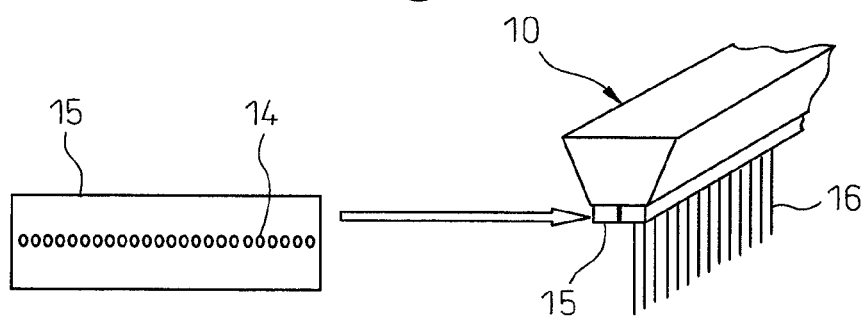
FIG. 4 shows a plan view of a nozzle plate comprising jet holes and an oblique view of the jet nozzle incorporating it.

As an example of a jet nozzle that can produce a bulky absorbent sheet having a concavoconvex pattern with one or more low density regions and one or more high density regions, FIG. 4 shows a plan view of a nozzle plate 15 with jet holes 14 and an oblique view of a jet nozzle 10 incorporating the same. Using the nozzle plate 15 shown in FIG. 4 produces a columnar jet 16.

Figure 5:
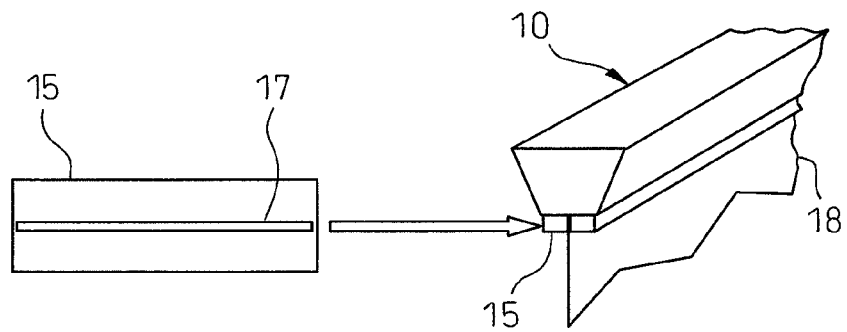
FIG. 5 shows a plan view of a nozzle plate comprising a spray slit and an oblique view of the jet nozzle incorporating it.

As another example of the aforementioned jet nozzle, FIG. 5 shows a plan view of a nozzle plate 15 comprising a spray slit 17, and an oblique view of a jet nozzle 10 incorporating it. Using the nozzle plate 15 shown in FIG. 5 produces a curtain jet 18.

Figure 6:
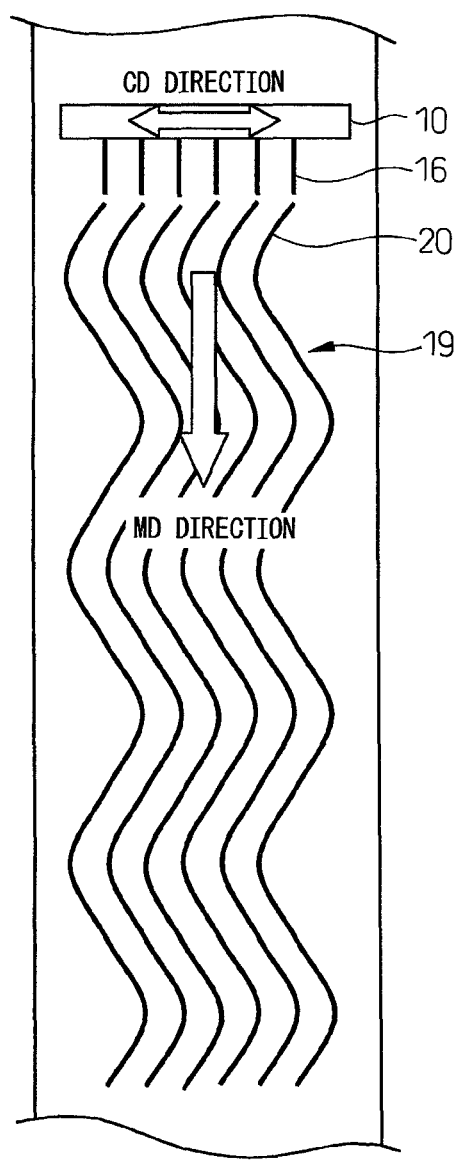
FIG. 6 shows wavy lines created by reciprocal movement of the jet nozzle in the CD direction.

When the jet nozzle 10 shown in FIG. 4 is used to spray moist hot air or water vapor onto a wet blended sheet by a columnar jet 16, the jet nozzle 10 may be fixed, or the jet nozzle 10 may be reciprocally moved in the CD direction of the wet blended sheet 1, to create a concavoconvex pattern of wavy lines 20 extending in the MD direction, as shown in FIG. 6.

Figure 7:
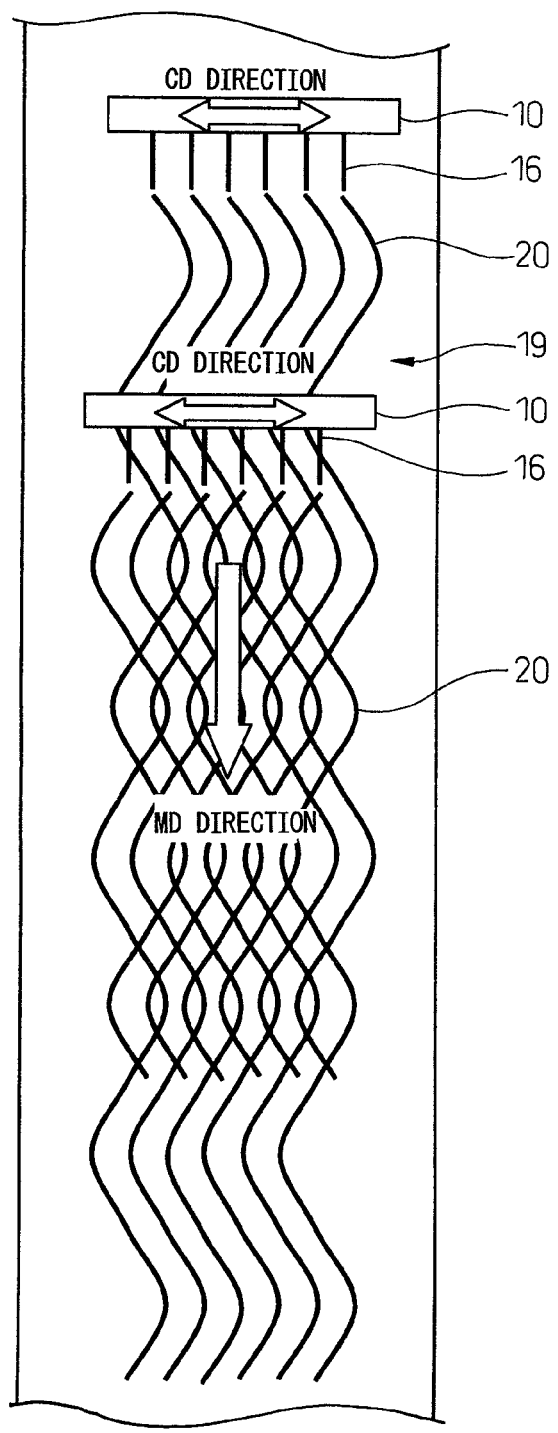
FIG. 7 shows wavy lines created by reciprocal movement of a multi-level jet nozzle in the CD direction.

FIG. 7 shows wavy lines created by reciprocal movement of a multi-level jet nozzle in the CD direction. If multiple jet nozzles 10 are provided as shown in FIG. 7, it is possible to form an interlaced pattern with crossed wavy lines 20. The pitch and heights of the waves are determined by the number of strokes (per minute) of the jet nozzle in the CD direction and the running speed (m/min) of the sheet in the MD direction. If multiple jet nozzles are provided, various different patterns can be produced by altering the stroke distance and cycle for each of the jet nozzles.

As used herein, "MD direction" means the machine direction during production, and "CD direction" means the cross machine direction perpendicular to the machine direction.

The density in the low density regions of the bulky absorbent sheet used for the invention is preferably 0.01 g/cm$^3$-0.1 g/cm$^3$ and more preferably 0.01 g/cm$^3$-0.05 g/cm$^3$, and the density in the high density regions is preferably 0.1 g/cm$^3$-0.3 g/cm$^3$.

When the bulky absorbent sheet has low density regions and high density regions, the term "density" used alone will refer to the apparent density of the bulky absorbent sheet.

If the density in the low density regions of the bulky absorbent sheet used for the invention is greater than 0.1 g/cm$^3$, the fluid retention property, deformation resistance and deformation stability will be reduced, while if it is less than 0.01 g/cm$^3$ the strength will be reduced and tearing will easily occur, tending to cause problems with surface friction durability. If the density of the high density regions of the bulky absorbent sheet is less than 0.1 g/cm$^3$ the fluid diffusibility will be impaired, and if it exceeds 0.3 g/cm$^3$, the heat-expanding particles will be in a virtually unexpanded state, such that absolutely none of the properties from the bulky absorbent sheet will be obtained.

A bulky absorbent sheet having a concavoconvex pattern comprising partial low-basis-weight regions with a low paper-making starting material content and partial high-basis-weight regions with a high paper-making starting material content, can be produced by using a partially blocked wire to obtain a wet blended sheet comprising partial low-basis-weight regions with a low paper-making starting material content and partial high-basis-weight regions with a high paper-making starting material content.

Figure 8:
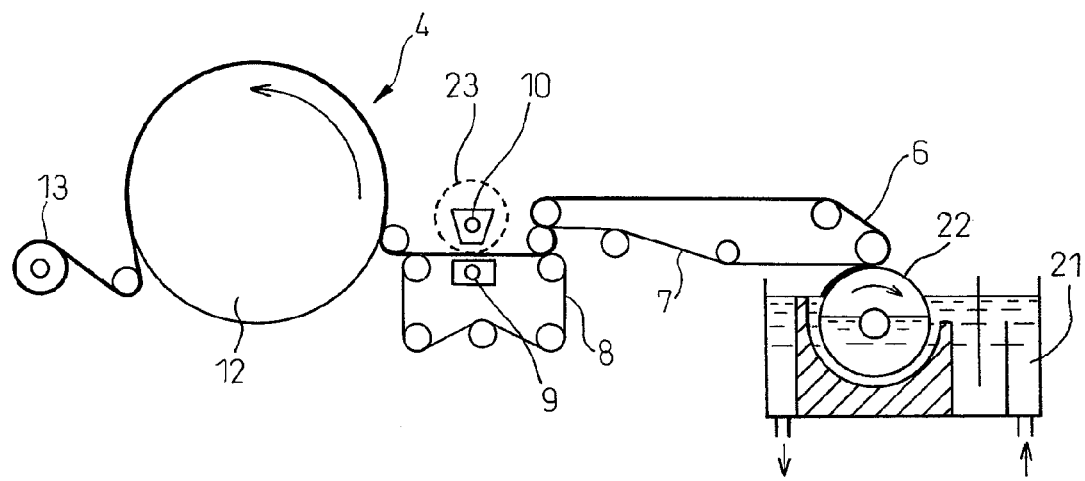
FIG. 8 is a schematic view of a paper machine that can produce a bulky absorbent sheet to be used for the invention.
Figure 9:
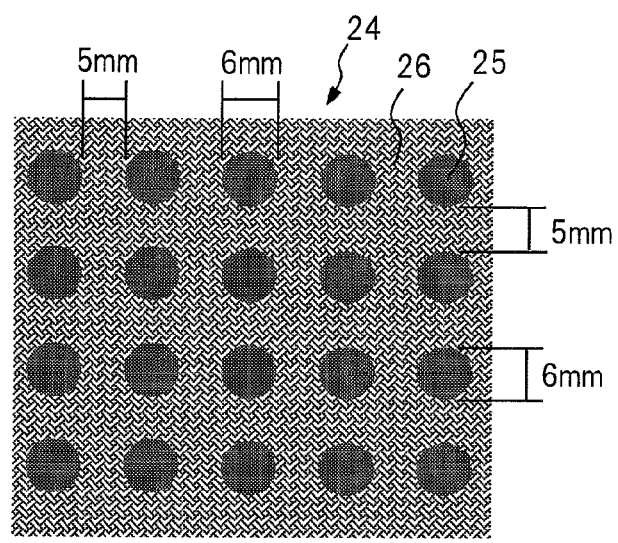
FIG. 9 is a plan view of paper-making wire for obtaining a bulky absorbent sheet having multiple low-basis-weight regions interspersed within high-basis-weight region.
Figure 10:
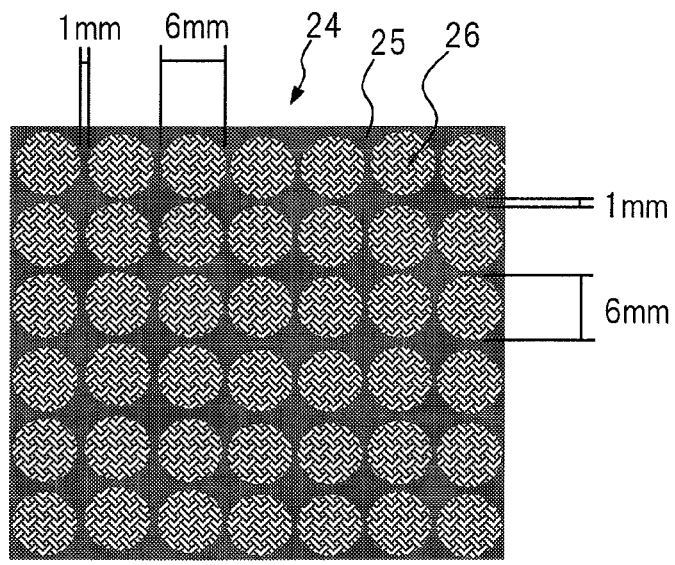
FIG. 10 is a plan view of paper-making wire for obtaining a bulky absorbent sheet having multiple high-basis-weight regions interspersed within low-basis-weight region.
Figure 11:
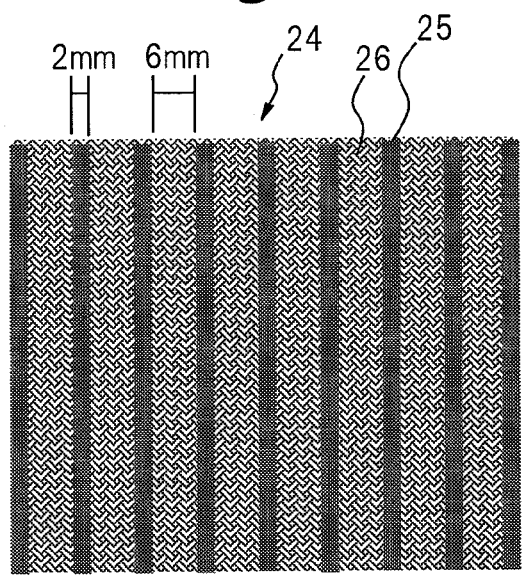
FIG. 11 is a plan view of paper-making wire for obtaining a bulky absorbent sheet having multiple high-basis-weight regions and multiple low-basis-weight regions arranged as lines in an alternating fashion in one direction.

To produce a bulky absorbent sheet having a concavoconvex pattern comprising one or more low-basis-weight regions and one or more high-basis-weight regions, there may be used the paper machine illustrated in FIG. 8 and the partially blocked paper-making wire 24, such as shown in FIGS. 9 to 11. When a partially blocked wire is used, it is possible to obtain a wet blended sheet comprising partial low-basis-weight regions with a low paper-making starting material content and partial high-basis-weight regions with a high paper-making starting material content. Specifically, water penetrates poorly at the blocked sections and therefore the paper-making starting material does not easily accumulate, thus forming partial low-basis-weight regions with a low paper-making starting material content, while water penetrates readily at the non-blocked sections and therefore the paper-making starting material easily accumulates, thus forming partial high-basis-weight regions with a high paper-making starting material content.

As used herein, partial regions with a low paper-making starting material content and a lower basis weight than the average basis weight will be referred to as "a low-basis-weight region", and partial region with a high paper-making starting material content and a higher basis weight than the average basis weight will be referred to as "a high-basis-weight region". If the heat-expanding particles are evenly dispersed in the paper-making starting material as according to the invention, the heat-expanding particles will be present in about the same proportion in the low-basis-weight regions and high-basis-weight regions, so that heating will cause expansion to produce bulk in both by the same proportion. The apparent bulk of the paper in the high-basis-weight regions having a higher basis weight than the average basis weight is larger than the average bulk, while the low-basis-weight regions are the opposite. It is therefore possible to obtain a bulky absorbent sheet with high apparent bulk in a large concavoconvex pattern.

The paper machine 4 of FIG. 8 comprises a paper-making starting material solution 21, a paper-making cylinder 22, a wet blended sheet 6, a first conveyor belt 7, a second conveyor belt 8, a suction box 9, a jet nozzle 10, a screen drum 23, a dryer 12 and a finished product take-up roll 13. A paper-making wire 24 is also mounted on the paper-making cylinder 22.

The paper-making cylinder 22 and paper-making wire 24 are used to produce a wet blended sheet 6 comprising one or more high-basis-weight regions and one or more low-basis-weight regions from a paper-making starting material solution 21 obtained by dispersing a fiber starting material and heat-expanding particles in water, wherein the wet blended sheet 6 is conveyed by a first conveyor belt 7 and a second conveyor belt 8, the wet blended sheet 6 is subsequently heated by hot air, moist hot air or water vapor from the jet nozzle 10 to cause expansion of the heat-expanding particles, the sheet is then dried if desired with the dryer 12, and the finished bulky absorbent sheet is taken up with the finished product take-up roll 13 to obtain a bulky absorbent sheet with a concavoconvex pattern.

Blocking of the paper-making wire 24 can be accomplished using a reaction curing resin or the like, and the sizes, number, shapes and arrangement thereof may be freely designed. For example, as shown in FIG. 9, the blocked regions 25 may be interspersed in the non-blocked regions 26, as shown in FIG. 10, the non-blocked regions 26 may be interspersed in the blocked regions 25, or as shown in FIG. 11, linear blocked regions 25 and linear non-blocked regions 26 may be arranged in an alternating fashion.

Low-basis-weight regions do not form as easily with a smaller single blocking size, while low-basis-weight regions form more easily at larger sized sections. If the size of a single blocked region is too small, the blocked sections will become covered with the paper-making starting material, filling in the blocked sections and thus preventing formation of low-basis-weight regions. On the other hand, if the size of a single blocked region is too large, uniform low-basis-weight regions will not form but rather open sections without paper-making starting material will tend to be created, resulting in easier tearing at the open sections during movement from the paper-making wire to the conveyor belt, thus impeding movement.

The optimum range for the size of a single blocked region cannot be specified since it will vary depending on the basis weight of the sheet. The area ratio of the blocked sections with respect to the total wire may be varied as necessary, but a larger area ratio is more effective for improving the apparent bulk of the sheet, whereas a smaller one reduces the apparent bulk. If the area ratio is too large, the starting material will concentrate excessively at the non-blocked sections during paper making, thus interfering with production of the sheet. The area ratio of the blocked sections with respect to the total wire will vary depending on the shapes of the blocked regions, but it may be 10%-60% and preferably 20%-50%.

In the paper-making wire 24 shown in FIG. 9, for example, the blocked regions 25 may be circles with diameters of 6 mm, and the distance between each blocked region 25 may be 5 mm. The remaining sections are the non-blocked regions 26. In the paper-making wire 24 shown in FIG. 10, for example, the non-blocked regions 26 may be circles with diameters of 6 mm, and the distance between each non-blocked region 26 may be 1 mm. The remaining sections are the blocked regions 25. In the paper-making wire 24 shown in FIG. 11, for example, the blocked regions 25 may be rectangles with widths of 2 mm, and the distance between each blocked region 25 may be 6 mm. The remaining sections are the non-blocked regions 26.

Figure 12:
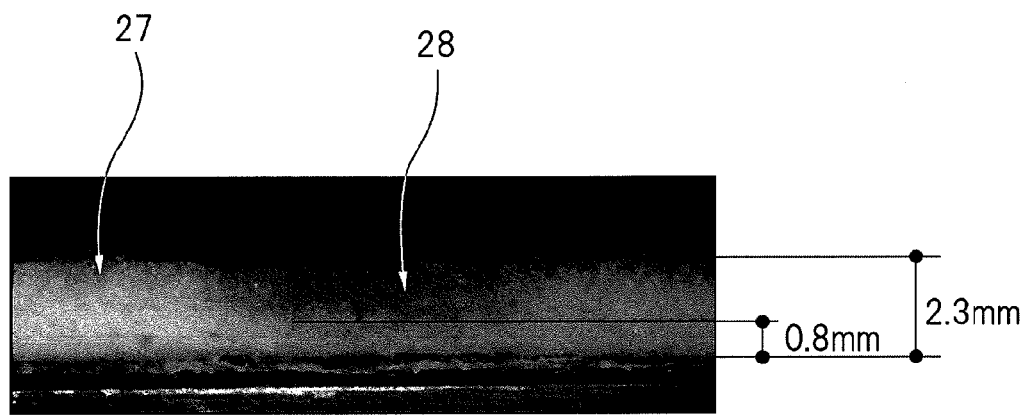
FIG. 12 shows an example of a bulky absorbent sheet produced by the paper machine shown in FIG. 8.

FIG. 12 shows an example of a bulky absorbent sheet produced by the paper machine 4 shown in FIG. 8. The bulky absorbent sheet produced by the paper machine 4 shown in FIG. 8 has high-basis-weight regions 27 and low-basis-weight regions 28.

The low-basis-weight regions have rapid fluid penetration, and therefore when it momentarily receives a large amount of body fluid, the fluid does not flow over the front side of the absorbent body but penetrates through to the lower layer. Since the one or more low-basis-weight regions are dispersed among the high-basis-weight region, there is essentially no reduction in the sheet strength as a whole. By providing one or more low-basis-weight regions, it is possible to further increase the basis weight of the one or more high-basis-weight regions, further increase the thickness of the one or more high-basis-weight regions compared to homogeneity, and to produce an excellent effect of preventing return of fluids and excellent cushioning properties. In consideration of the fluid permeation effect, the size of each low-basis-weight region is preferably such that the diameter or side length is 1 mm-5 mm. If it is less than 1 mm, the resistance will be too great during fluid permeation, and if it exceeds 5 mm, fluid will tend to flow back from the lower layer.

From the viewpoint of fluid absorption rate, fluid diffusibility and absorbed fluid retention volume, the bulky absorbent sheet used for the invention has a Klemm water absorption degree, described hereunder, of preferably 10 mm or greater, more preferably 30 mm or greater and even more preferably 40 mm or greater.

From the viewpoint of fluid retention, the bulky absorbent sheet used for the invention has a percentage reduction in wet compressive bulk (%), also described hereunder, of preferably no greater than 50% and more preferably no greater than 40%.

From the viewpoint of fluid retention, the bulky absorbent sheet used for the invention has a wet compressive residual strain (%), also described hereunder, of preferably no greater than 30%, more preferably no greater than 20% and even more preferably no greater than 15%.

Examples for the top sheet include known nonwoven fabrics, such as through-air nonwoven fabrics, point bond nonwoven fabrics, spunlace nonwoven fabrics, spunbond nonwoven fabrics, spunbond/meltblown/spunbond nonwoven fabrics and meltblown nonwoven fabrics, and liquid-permeable materials, such as porous films.

Examples for the back sheet include non-water-permeable film materials produced from polyethylene or polypropylene resins, moisture-permeable film materials containing inorganic filler materials, and water-permeable sheet materials used in the top sheet. There may also be mentioned poromeric films, non-poromeric films, porous films and the like made from high-density polyethylene/low-density polyethylene.

As used herein, "skin-contacting surface" refers to the side that contacts the skin during wearing, while "non-skin-contacting surface" refers to the surface on the side that does not contact the skin during wearing, which is, for example, the side that contacts underwear if the absorbent article is a sanitary napkin.

Various forms may be selected for the absorbent body used for the invention, including the bulky absorbent sheet described above, according to the purpose of the product. For example, the absorbent body to be used for the invention may be composed of a single type of bulky absorbent sheet, or it may have a built-up structure, being composed of 2 or more bulky absorbent sheet layers with different densities or basis weights. Also, the absorbent body may have a built-up structure with a bulky absorbent sheet and another material, such as a fluff pulp mat, absorbent sheet, dry pulp nonwoven fabric or other nonwoven fabric, and/or a super-absorbent polymer.

When the absorbent body used for the invention has a built-up structure, most preferably the uppermost layer on the top sheet side is the bulky absorbent sheet layer. This will allow the properties, and especially the fluid diffusibility, of the bulky absorbent sheet of the invention to be exhibited.

As used herein, "interlayer" refers to a layer in a 3-layer built-up structure other than the uppermost layer on the top sheet and the lowermost layer on the back sheet side.

Figure 13:
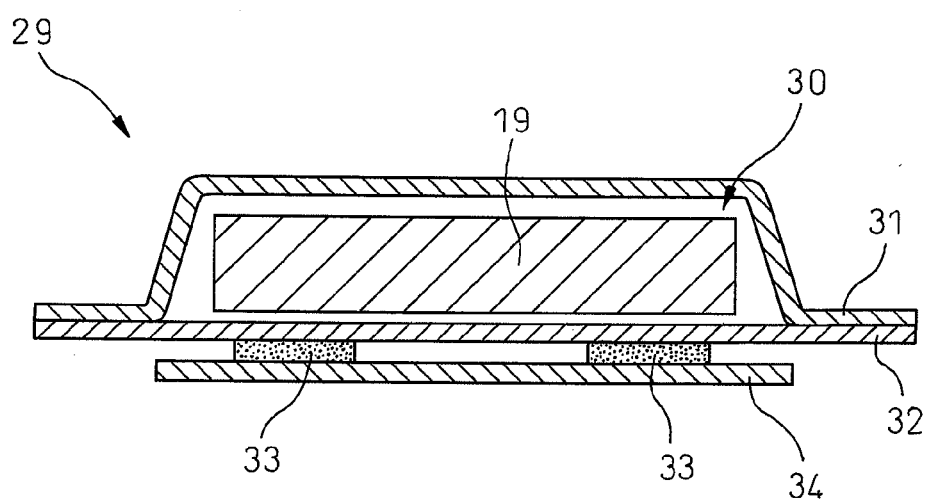
FIG. 13 is a cross-sectional view of an embodiment of an absorbent article of the invention.

FIG. 13 is a cross-sectional view of an embodiment of an absorbent article of the invention. The absorbent article 29 shown in FIG. 13 comprises a top sheet 31 on the skin contact side, a back sheet 32 on the non-skin contact side, and an absorbent body 30 positioned between these two sheets. The absorbent article 29 shown in FIG. 13 also has a cohesive part 33 and a detached portion 34 on the non-skin contact side of the back sheet 32. When the absorbent article is a sanitary napkin, for example, the absorbent article 29 is anchored to underwear by the cohesive part 33.

The absorbent body 30 in FIG. 13 is composed of a bulky absorbent sheet 19.

FIG. 14 shows a variation example of an absorbent article of the invention, wherein the absorbent body has a multilayer structure. In FIG. 14(*a*), the absorbent body 30 comprises a bulky absorbent sheet 19 layer, a super-absorbent polymer 35 layer and a water-resistant tissue paper 36 layer, in that order from the top sheet 31 side. In FIG. 14(*b*), the absorbent body 30 comprises a bulky absorbent sheet 19 layer, a super-absorbent polymer 35 layer and a bulky absorbent sheet 19' layer, in that order from the top sheet 31 side. The bulky absorbent sheets 19 and 19' may be the same bulky absorbent sheet, or they may be different bulky absorbent sheets. In FIG. 14(*c*), the absorbent body 30 comprises a bulky absorbent sheet 19 layer and a flap pulp layered mat 37, in that order from the top sheet 31 side. In FIG. 14(*c*), the bulky absorbent sheet 19 layer has a smaller size, than the flap pulp layered mat 37 layer.

With the construction shown in FIG. 14(*a*), the bulky absorbent sheet 19 layer which has an excellent fluid absorption rate and excellent fluid diffusibility and moist deformation stability, rapidly absorbs fluid and can transmit it to the super-absorbent polymer 35 layer which has excellent absorbed fluid retention volume and fluid retention but has a slow absorption rate, while the twisting deformation of the absorbent body can also be reduced, to yield an absorbent article with low leakage.

With the construction shown in FIG. 14(*b*), the bulky absorbent sheet 19 layer which has an excellent fluid absorption rate and excellent fluid diffusibility and moist deformation stability, rapidly absorbs fluid and can transmit it to the super-absorbent polymer 35 layer which has excellent absorbed fluid retention volume and fluid retention but has a slow absorption rate, and furthermore, fluid that has passed through without being absorbed by the super-absorbent polymer 35 layer can be absorbed by the underlying bulky absorbent sheet 19', which has excellent absorbed fluid retention volume and fluid retention, and deformation resistance is further increased by using a 2-layer bulky absorbent sheet, to yield an absorbent article with even lower leakage.

With the construction shown in FIG. 14(*c*), the bulky absorbent sheet 19 layer which has an excellent fluid absorption rate and excellent fluid diffusibility and moist deformation stability, is layered so as to cover the fluff pulp layered mat 37, which is more inexpensive and has an excellent fluid absorption rate and absorbed fluid retention volume but inferior moist form retention and fluid retention, and therefore it has excellent ability to momentarily absorb large amounts of fluid, and an absorbent article with minimal reverse flow of fluid and low twisting deformation can be inexpensively obtained, which is economical.

As used herein, "super-absorbent polymer" refers to a synthetic polymer-based absorber, such as a starch-based, cellulose-based, polyacrylic acid-based, polyvinyl alcohol-based, polyacrylamide-based or polyoxyethylene-based absorber. The super-absorbent polymer is preferably a polyacrylic acid-based absorber and more preferably a sodium polyacrylate-based absorber.

As used herein, "fluff pulp layered mat" refers to a mat in which a fluff pulp is laminated.

Also, as used herein, "water-resistant tissue paper" refers to tissue paper with a wet tensile strength of 0.6 N/25 mm or greater in both the MD direction and CD direction. The wet tensile strength can be measured according to JIS P 8135.

When the fiber of the bulky absorbent sheet in the absorbent article of the invention has a pulp body, the pulp is easily softened by absorption of moisture upon being worn, and then the expanded heat-expanding particles serve the role of a sponge cushion, thus providing a satisfactory feel during wear.

The absorbent article of the invention may be a panty liner, sanitary napkin, paper diaper, perspiration sheet, pet sheet, or absorbing sheet for drip of foods, such as meat or fish.

EXAMPLES

The invention will now be explained in greater detail using examples and comparative examples, with the understanding that the invention is in no way limited by the examples.
—Production of Bulky Absorbent Sheet 1—

After (i) 70 parts by mass of unbeaten Northern bleached Kraft pulp and 15 parts by mass of 2.2 dtex×5 mm PP/PE core-sheath composite fiber (NBF, product of Daiwabo Polytec Co., Ltd.) as fiber starting materials, (ii) 15 parts by mass of low-boiling-point solvent-encapsulating microcapsules (FUC-36 Matsumoto Microspheres, product of Matsumoto Yushi-Seiyaku Co., Ltd., particle size: 5-15 μm, initial expansion temperature: 75-85° C.) as heat-expanding particles, and (iii) as auxiliary agents, 0.5 part by mass (as the active ingredient) of a cation-modified acrylic copolymer (FILEX RC-104 by Meisei Chemical Works, Ltd.) and 0.3 part by mass (as the active ingredient) of an acrylic copolymer (FILEX M by Meisei Chemical Works, Ltd.), as agents for anchoring the heat-expanding particles to the pulp, 0.5 part by mass (as the active ingredient) of a polyamide/epichlorhydrin resin (WS4024, wet strength agent by Seiko PMC Corp.) as a paper strength additive, and 0.4 part by mass (as the active ingredient) of a fatty acid amide (PROSOFT TQ218 by Hercules, Inc.) as a hydrophilic flexibilizer, were mixed in water an aqueous dispersion was formed to obtain a 2 mass % paper-making starting material 1. The paper machine shown in FIG. 3 was used for paper-making using the obtained paper-making starting material 1, and the heat-expanding particles were thermally expanded and dried while heating with a yankee dryer, to obtain a bulky absorbent sheet 1 with a basis weight of 50 g/m$^2$, a thickness of 0.75 mm and a density of 0.067 g/cm$^3$.

FIG. 1 shows an electron micrograph of the front side of the bulky absorbent sheet 1, and FIG. 2 shows an electron micrograph of a cross-section of the bulky absorbent sheet 1. In FIG. 1 and FIG. 2, numeral 1 denotes an expanded expanding particle, numeral 2 denotes the fiber starting material, and numeral 3 denotes an expanded heat-expanding particle.
—Production of Bulky Absorbent Sheet 2—

The paper-making starting material 1 produced in Production Example 1 was used for paper-making with the paper machine shown in FIG. 3, and the prepared wet blended sheet was sprayed with steam from a jet nozzle to thermally expand the heat-expanding particles, after which the wet blended sheet containing the expanded heat-expanding particles was dried with a dryer to obtain a bulky absorbent sheet 2 having a basis weight of 50 g/m$^2$, a thickness of 1.6 mm and a density of 0.031 g/cm$^3$.
—Preparation of Comparative Absorbent Sheet 1—

A commercially available dry pulp nonwoven fabric (KINOCLOTH, product of Oji Kinocloth Co., Ltd., basis weight: 48 g/m$^2$, thickness: 1.05 mm, density: 0.046 g/cm$^3$) was prepared, for use as a comparative absorbent sheet 1. The dry pulp nonwoven fabric was a nonwoven fabric produced by spraying an acrylic resin emulsion binder onto a fibrous mat obtained by laminating dry macerated pulp fiber, and then drying it.
—Production of Comparative Absorbent Sheet 2—

A comparative absorbent sheet 2 was produced by the same process as Production Example 1, except for excluding the low-boiling-point solvent-encapsulating microcapsules (Matsumoto Microsphere FUC-36 by Matsumoto Yushi-Seiyaku Co., Ltd.) as the heat-expanding particles and the cation-modified acrylic copolymer (FILEX RC-104 by Meisei Chemical Works, Ltd.) and the acrylic copolymer (FILEX M by Meisei Chemical Works, Ltd.), as the agents for anchoring the heat-expanding particles to the pulp.
—Production of Absorbent Article 1—

An air-through nonwoven fabric (basis weight: 35 g/m$^2$) comprising PE/PET sheath/core composite fibers (2.2 dtex, 51 mm) as a top sheet, a bulky absorbent sheet 1 as an absorbent body and a PE film (basis weight: 35 g/m$^2$) as a back sheet were prepared. The absorbent body was bonded to the top sheet and back sheet with a hot-melt adhesive, and the ends of the top sheet and back sheet were bonded with a hot-melt adhesive, to produce an absorbent article 1 as shown in FIG. 13.
—Production of Comparative Absorbent Article 1—

A comparative absorbent article 1 was produced in the same manner as Production Example 5, except for using the comparative absorbent sheet 1 prepared in Production Example 3 as the absorbent body instead of the bulky absorbent sheet 1.

The performance of the bulky absorbent sheets 1 and 2 and the comparative absorbent sheets 1 and 2 was evaluated by the following test methods.
(1) Dry tensile strength: JIS P 8113.
(2) Wet tensile strength; JIS P 8135.
(3) Bending resistance: JIS L 1096, method A.
(4) Klemm water absorption degree: Evaluated according to JIS P 8141, as the wicking height (mm) in 1 minute.
(5) Percentage reduction in wet compressive bulk: The initial thickness $T_0$ is measured after absorption of a 6-fold amount of water by mass in the measuring sample. Next, a weight with a 10 cm×10 cm base and a weight of 3.5 kg is placed on the water-absorbed specimen for 5 minutes, the thickness $T_1$ under the weight is measured, and the percentage reduction in wet compressive bulk is measured according to the following formula.

Percentage reduction in wet compressive bulk (%)= $(T_0-T_1) \div T_0 \times 100$ (6) Wet compressive residual strain: After measurement of the percentage reduction in wet compressive bulk, the weight is removed, the thickness $T_2$ of the specimen is measured after 5 minutes have elapsed, and the wet compressive residual strain is measured according to the following formula.

Wet compressive residual strain (%)=$(T_0-T_2) \div T_0 \times 100$

Measurement of $T_0$, $T_1$ and $T_2$ was performed with a microscope.

The results are shown in Table 1, FIG. 15 shows a telescope image of a cross-section of the specimen during measurement of the percentage reduction in wet compressive bulk, and FIG. 16 shows a telescope image of a cross-section of the specimen during measurement of the wet compressive residual strain.

FIG. 15(a) and FIG. 16(a) are images of the bulky absorbent sheet 1, FIG. 15(b) and FIG. 16(b) are images of the bulky absorbent sheet 2, and FIG. 15(c) and FIG. 16(c) are images of the comparative absorbent sheet 1. In FIG. 15 and FIG. 16, numeral 38 denotes the weight and numeral 39 denotes the sample.

TABLE 1

|  |  | Production Example 1 Bulky absorbent sheet 1 | Production Example 2 Bulky absorbent sheet 2 | Production Example 3 Comparative absorbent sheet 1 | Production Example 4 Comparative absorbent sheet 2 |
|---|---|---|---|---|---|
| Basis weight (g/m²) |  | 50.1 | 50.0 | 50.9 | 48.0 |
| Thickness (mm) |  | 0.75 | 1.60 | 0.12 | 1.05 |
| Density (g/cm³) |  | 0.067 | 0.031 | 0.424 | 0.046 |
| Dry tensile | MD | 11.27 | — | 34.12 | 5.34 |
| strength (N/25 mm) | CD | 9.96 | — | 35.50 | 3.96 |
| Moist tensile | MD | 3.70 | — | 8.73 | 2.35 |
| strength (N/25 mm) | CD | 3.15 | — | 10.36 | 1.87 |
| Dry bending | MD | 170 | — | 85 | 113 |
| resistance (mm) | CD | 138 | — | 77 | 85 |
| Wet bending | MD | 41 | — | 0 | 28 |
| resistance (mm) | CD | 41 | — | 0 | 10 |
| Klemm water | MD | 41 | — | 11 | 5 |
| absorption degree (mm) | CD | 40 | — | 10 | 4 |
| Percentage reduction in wet compressive bulk (%) |  | 37 | 14 | — | 54 |
| Wet compressive residual strain (%) |  | 10 | 7 | — | 39 |

Table 1 suggests that the absorbent body used for the invention has a high Klemm water absorption degree and an excellent fluid absorption rate and fluid diffusibility. In addition, it suggests that the absorbent body used for the invention has low percentage reduction in wet compressive bulk and low wet compressive residual strain, as well as excellent fluid retention, and high deformation resistance and shape stability.

The performance of the absorbent article 1 and comparative absorbent article 1 was evaluated by the following test methods.

(7) Diffusibility: After dropping 0.5 g of artificial menstrual blood onto the center section of the top sheet of the absorbent article, and allowing it to stand for 1 minute or 10 minutes, the diffusion dimension of the artificial menstrual blood is measured in the lengthwise direction of the absorbent article and in the direction perpendicular to the lengthwise direction.

(8) Rewetting rate: Filter paper was placed on the top sheet of the absorbent article after measuring the diffusion dimension upon standing for 1 minute and for 10 minutes, a weight was placed on the filter paper for a load of 30 g/cm², the mass m(g) of the artificial menstrual blood absorbed by the filter paper after standing for 1 minute and for 10 minutes was measured, and the rewetting rate was calculated by the following formula.

Rewetting rate (%)=$m \div 0.5 \times 100$

Figure 17:
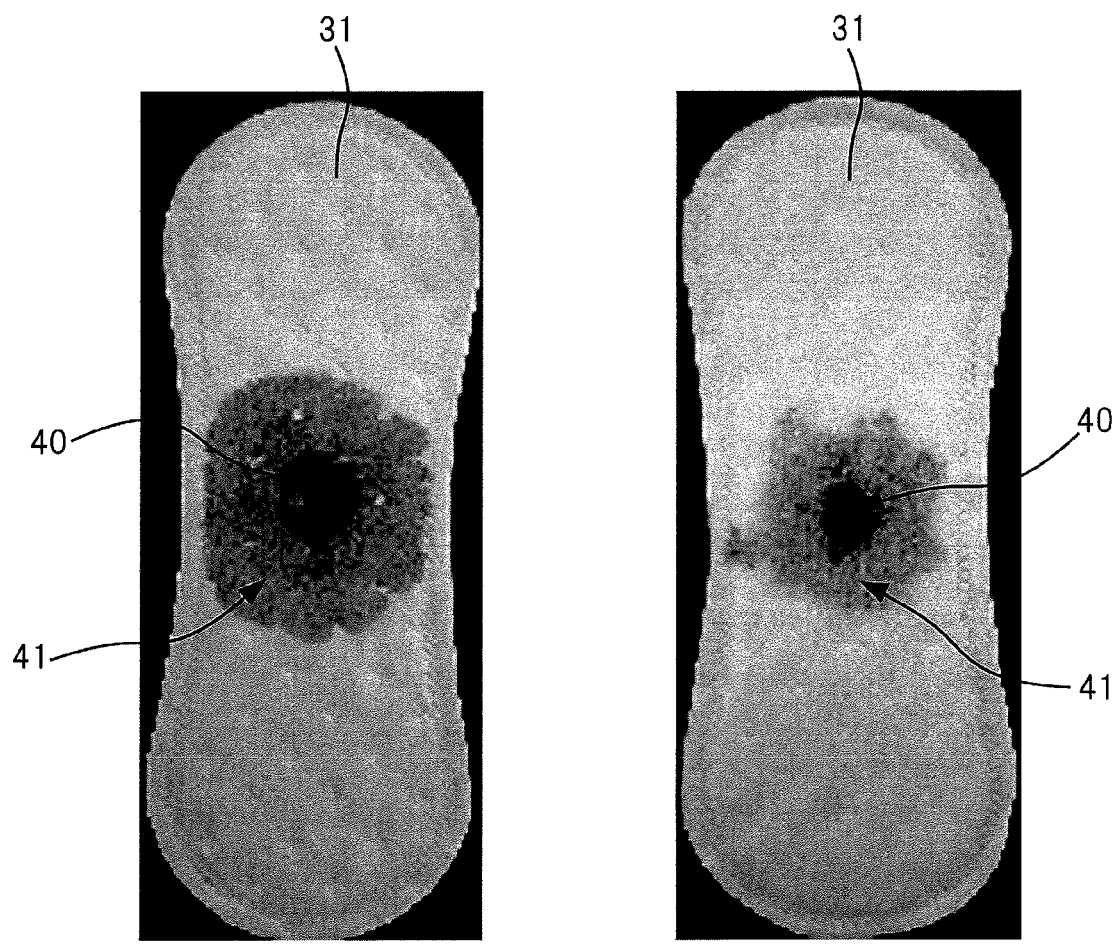
FIG. 17 shows an image of an absorbent article 1 after the diffusibility test (standing for 10 minutes after dropping artificial menstrual blood), and a comparative absorbent article 1, for Example 2.

The results are shown in Table 2, and FIG. 17 shows an image of the absorbent article 1 and the comparative absorbent article 1 after the diffusibility test (standing for 10 minutes after dropping artificial menstrual blood). In FIG. 17, numeral 40 denotes fluid diffusion into the top sheet 31, and numeral 41 denotes fluid diffusion into the absorbent body.

TABLE 2

|  | 1 minute after dropping ||| 10 minutes after dropping |||
|---|---|---|---|---|---|---|
|  | Fluid diffusibility (mm × mm) || Rewetting rate (%) | Fluid diffusibility (mm × mm) || Rewetting rate (%) |
|  | Top sheet | Absorbent body |  | Top sheet | Absorbent body |  |
| Absorbent article 1 | 17 × 14 | 47 × 38 | 44.5 | 16 × 12 | 56 × 41 | 27.9 |
| Comparative absorbent article 1 | 10 × 11 | 35 × 36 | 73.9 | 10 × 9 | 35 × 40 | 68.4 |

The absorbent article of the invention has high fluid diffusibility in the absorbent body. The absorbent article of the invention also has a low rewetting rate and excellent fluid retention.

REFERENCE SIGNS LIST

1 Expanded heat-expanding particles
2 Fiber starting material
3 Cross-section of expanded heat-expanding particles
4 Paper machine
5 Paper-making part
6 Wet blended sheet
7 First conveyor belt
8 Second conveyor belt
9 Suction box
10 Jet nozzle
11 Screen
12 Dryer
13 Finished product take-up roll
14 Jet hole
15 Nozzle plate
16 Columnar jet
17 Spray slit
18 Curtain jet
19,19' Bulky absorbent sheets
20 Wavy line
21 Paper-making starting material solution
22 Paper-making cylinder
23 Screen drum
24 Paper-making wire
25 Blocked region
26 Non-blocked region
27 High-basis-weight region
28 Low-basis-weight region
29 Absorbent article
30 Absorbent body
31 Top sheet 32 Back sheet
33 Cohesive part
34 Detached portion
35 Super-absorbent polymer
36 Water-resistant tissue paper
37 Fluff pulp layered mat
38 Weight
39 Sample
40 Fluid diffusion in top sheet
41 Fluid diffusion in absorbent body

The invention claimed is:

1. An absorbent article comprising a top sheet on the skin contact side, a back sheet on the non-skin contact side, and an absorbent body situated between the two sheets:
   wherein the absorbent body comprises a bulky absorbent sheet, and
   the bulky absorbent sheet comprises heat-expanding particles that are dispersed in the bulky absorbent sheet and have been expanded by heat,
   wherein the bulky absorbent sheet has a density of 0.025-0.1 g/cm$^3$ and comprises:
   a blended sheet comprising the heat-expanding particles dispersed in a fiber starting material from a paper-making starting material, in which the fiber starting material comprising 30-100 mass % of natural pulp and 0-70 mass % of other fiber, and the heat-expanding particles having an initial mean particle size of 5-30 μm are dispersed at a proportion of 5-30 parts by mass of the heat-expanding particles having the initial particle size per 100 parts by mass of the fiber starting material, and in which at least some of the heat-expanding particles being expanded by heat to a 20-125 fold volume,
   wherein the Klemm water absorption degree of the bulky absorbent sheet is at least 10 mm, the percentage reduction in wet compressive bulk is no greater than 50%, and the wet compressive residual strain is no greater than 30%.

2. The absorbent article according to claim 1, wherein the heating is carried out by moist hot air or water vapor.

3. The absorbent article according to claim 1, wherein the bulky absorbent sheet has a concavoconvex pattern consisting of one or more high-basis-weight regions having a basis weight higher than the average basis weight and one or more low-basis-weight regions having a basis weight lower than the average basis weight.

4. The absorbent article according to claim 3, wherein the one or more low-basis-weight regions are interspersed within the high-basis-weight region.

5. The absorbent article according to claim 1, wherein the bulky absorbent sheet has a concavoconvex pattern consisting of one or more low density regions having a density of 0.01-0.1 g/cm$^3$ and one or more high density regions having a density of 0.1-0.3 g/cm$^3$, and the one or more low density regions has a degree of expansion of the heat-expanding particles higher than that of the one or more high density regions.

6. The absorbent article according to claim 1, wherein the absorbent body has a multilayer structure, and the uppermost layer on the top sheet side is the bulky absorbent sheet layer.

7. The absorbent article according to claim 6, wherein the multilayer structure is composed of 3 or more layers, and at least one of the interlayers is a super-absorbent polymer layer.

8. The absorbent article according to claim 7, wherein the lowermost layer is the bulky absorbent sheet or water-resistant tissue paper layer.

* * * * *